(12) United States Patent
Wang et al.

(10) Patent No.: US 10,561,791 B2
(45) Date of Patent: Feb. 18, 2020

(54) SYRINGE, AND DEVICE FOR RAPIDLY LOADING AND RELEASING THE SAME

(71) Applicant: Suzhou Hengrui Disheng Medical Co., Ltd, Suzhou (CN)

(72) Inventors: Jun Wang, Suzhou (CN); Guofeng Kan, Suzhou (CN); Pengcheng Long, Suzhou (CN)

(73) Assignee: Suzhou Hengrui Disheng Medical Co., Ltd., Suzhou (CN)

( * ) Notice: Subject to any disclaimer, the term of this patent is extended or adjusted under 35 U.S.C. 154(b) by 197 days.

(21) Appl. No.: 15/825,827

(22) Filed: Nov. 29, 2017

(65) Prior Publication Data

US 2018/0304015 A1    Oct. 25, 2018

(30) Foreign Application Priority Data

Apr. 21, 2017  (CN) .......................... 2017 1 0268907
Apr. 21, 2017  (CN) ................... 2017 2 04295928 U

(51) Int. Cl.
*A61M 5/20*    (2006.01)
*A61M 5/145*    (2006.01)

(52) U.S. Cl.
CPC ...... *A61M 5/2033* (2013.01); *A61M 5/14546* (2013.01); *A61M 2005/14573* (2013.01); *A61M 2005/2073* (2013.01)

(58) Field of Classification Search
CPC ............ A61M 5/2033; A61M 5/14546; A61M 2005/14573; A61M 2005/2073; A61M 2005/2488; A61M 2039/1033; A61M 5/31515; A61M 5/145; Y10S 128/01
USPC .......................................................... 604/135
See application file for complete search history.

(56) References Cited

U.S. PATENT DOCUMENTS

2001/0047153 A1* 11/2001 Trocki .............. A61M 5/14546
                                                              604/155

* cited by examiner

*Primary Examiner* — Bhisma Mehta
*Assistant Examiner* — Nidah M Hussain
(74) *Attorney, Agent, or Firm* — Muncy, Geissler, Olds & Lowe, P.C.

(57) ABSTRACT

A syringe and device for rapidly loading and releasing the syringe. A limiting flange and clamping flange are on a connection end of the syringe. The clamping flange is proximate to a rear end of the connection end and includes at least two clamping portions. The device includes an injection head, pushing ring, guide sleeve, and at least two bayonet locks. The bayonet locks are on the injection head by first elastic structures flexible along a radial direction. One end of the pushing ring stretches into the guide sleeve. A second elastic structure is between the pushing ring and guide sleeve. The other end of the pushing ring faces sides of the bayonet locks. Bump components are disposed on sides of the bayonet locks, with bump slots corresponding thereto. Clamping slots for insertion of the clamping portions are on an end face of the pushing ring.

15 Claims, 12 Drawing Sheets

SYRINGE, AND DEVICE FOR RAPIDLY LOADING AND RELEASING THE SAME

TECHNICAL FIELD

The present disclosure relates to the technical field of syringe design, and more particularly, relates to a syringe, and a device for rapidly loading and releasing the same.

BACKGROUND ART

A syringe is generally used with an injector. The syringe contains liquid. The syringe is connected to the injector, and the injector pushes the liquid in the syringe to implement injection.

An existing injector has a problem of inconvenient use regarding loading and releasing of the syringe, which may affect a manner of loading the syringe onto the injector and/or keeping the syringe inside the injector. The inconvenience of the design may complicate the way of loading and releasing of a user (for example, a care provider).

SUMMARY OF THE INVENTION

For the problem in the background, the present disclosure provides a syringe. A limiting flange and a clamping flange are disposed on an outer side wall of a connection end of the syringe, the clamping flange is approximate to a rear end of the connection end of the syringe, and the clamping flange includes at least two clamping portions that are disposed on the same circle.

Preferably, sides, facing away from the limiting flange, of the clamping portions are ramps.

Preferably, first chamfers are disposed on two ends of each side, facing away from the limiting flange, of the clamping portions.

The present disclosure provides a device for rapidly loading and releasing a syringe, used to rapidly load and release the syringe described above;
the device includes an injection head, at least two bayonet locks, a pushing ring, and a guide sleeve, both of the bayonet locks are on the same circle, and the bayonet locks are disposed on the injection head by means of first elastic structures in a manner of being movable along a radial direction; one end of the pushing ring stretches into the guide sleeve, and a second elastic structure is disposed between the pushing ring and the guide sleeve; the other end of the pushing ring faces sides of the bayonet locks, bump components are disposed on the sides of the bayonet locks, bump slots are disposed on locations, corresponding to the bump components, on an end surface of the other end of the pushing ring, the bump components stretch into the bump slots, the pushing ring rotates relative to the bayonet locks, and when the bump components slide along the bump slots, the bump components drive the bayonet locks to move along a radial direction; clamping slots used for insertion of clamping portions are further disposed on an end surface, facing the bayonet locks, of the pushing ring;
during loading, the syringe is inserted into the injection head, the clamping portions push the bayonet locks away, and the bayonet locks move outwards along a radial direction and act on the first elastic structures; after the clamping flange passes through the bayonet locks, the bayonet locks are restored under the action of the first elastic structures and abut on the outside of the syringe; a side of the clamping flange abuts on the side of the bayonet locks, and a side of the limiting flange abuts on an outer side wall of the injection head, so that the syringe is positioned along an axial direction; each clamping portion of the clamping flange stretches into a corresponding clamping slot; and during releasing, the syringe is rotated, and drives, by means of the clamping portions inside the clamping slots, the pushing ring to rotate, and the pushing ring rotates and acts on the second elastic structure; the pushing ring rotates, so the bump components move in the bump slots to drive the bayonet locks to move outwards along a radial direction, further the bayonet locks are disengaged from the clamping flange, and the syringe is pulled out along an axial direction; after the syringe is released, under the action of the second elastic structure, the pushing ring rotates and is restored.

Preferably, a socket used for insertion of the syringe is disposed on the injection head, and the ring of the socket and the bayonet locks located, the pushing ring, and the guide sleeve are disposed based on a same axis; loading slots are respectively disposed on locations, corresponding to the bayonet locks, on an edge of the socket, and the clamping portions enter the injection head through the loading slots.

Preferably, first chamfers are disposed on two ends of each of the clamping portions, and second chamfers matching the first chamfers are disposed on two ends of each of the loading slots.

Preferably, sides, facing the injection head, of the clamping portions are first ramps, and second ramps matching the first ramps are disposed on ends of the bayonet locks.

Preferably, the first set of slots are disposed on the injection head, each of the bayonet locks corresponds to one of the first set of slots, the bayonet locks are installed inside the first set of slots, one end of each of the bayonet locks stretches into one of the corresponding first set of slots and the first elastic structures are disposed between the bayonet locks and the first set of slots, and the bayonet locks move along the first set of slots along a radial direction.

Preferably, the bump components include embossed bearing shafts disposed on sides of the bayonet locks and bearings sleeved on the embossed bearing shafts.

Preferably, the bump slots are disposed along a circumferential direction, and each bump slot gradually deviates from the center from an initial end to a tail end.

Preferably, limiting bosses are disposed on the end, stretching into the guide sleeve, of the pushing ring, guide sleeve limiting slots are disposed inside the guide sleeve, the limiting bosses stretch into the guide sleeve limiting slots, the pushing ring rotates relative to the guide sleeve, and the limiting bosses slide along the guide sleeve limiting slots, to limit a range of an angle by which the pushing ring rotates.

Preferably, the second elastic structure is a torsion spring, the torsion spring is sleeved on an outer circle of the pushing ring, one end of the torsion spring is fixed onto the pushing ring, and the other end is fixed onto the guide sleeve.

Preferably, the clamping flange includes two clamping portions that are disposed symmetrically along a circumferential direction, and two bayonet locks disposed symmetrically along a circumferential direction are disposed on the injection head.

Preferably, two backing pins are further disposed on the injection head, the backing pins and the bayonet locks are disposed on the same circle, and the backing pins are disposed between adjacent bayonet locks; the second set of slots are disposed on the injection head, one end of each of the backing pins stretches into one of the corresponding second set of slots, third elastic structures are disposed between the backing pins and the second set of slots, and the other end stretches out from the one of the corresponding second set of slots; and during releasing of the syringe, after the bayonet locks move outwards, the syringe is moved outwards along an axial direction, the clamping portions push to enable the two backing pins to move outwards, the syringe is disengaged from the injection head, and then the backing pins are restored under the action of the third elastic structures.

Preferably, releasing slots are further disposed on locations, corresponding to the backing pins, on an edge of the socket on the injection head, and during releasing, after pushing to enable the backing pins to move outwards, the clamping portions slide out from the injection head along the releasing slots.

Preferably, the clamping flange includes four clamping portions, the four clamping portions are evenly arranged on the syringe along an axial direction, two bayonet locks are disposed on the injection head, and the two bayonet locks face two clamping portions that are disposed opposite to each other.

By means of the foregoing technical solutions, compared with the prior art, the present disclosure has the following advantages and positive effects:

By means of the device for rapidly loading and releasing a syringe provided in the present disclosure, an injector syringe having a special structure can be rapidly loaded onto the device and taken out as long as the syringe is rotated, so that an operation is convenient, and a structure is simple and compact. In addition, the syringe is connected to the device stably, and does not easily shake, thereby implementing stable connection to an injector.

BRIEF DESCRIPTION OF THE DRAWINGS

The foregoing and other features and advantages may be understood more clearly with reference to the accompany drawings by means of the following detailed descriptions, where.

DETAILED DESCRIPTION OF THE INVENTION

Figure 1:
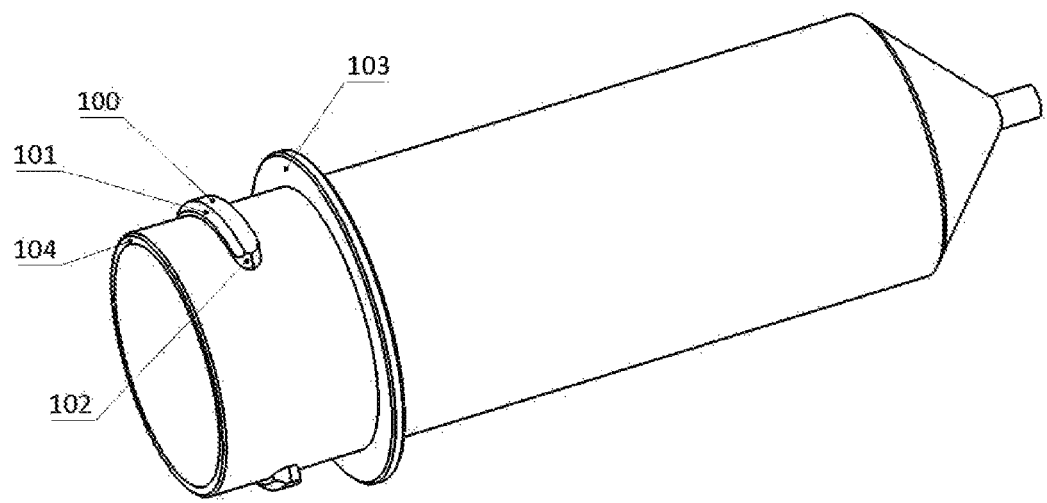
FIG. 1 is a schematic structural diagram of a syringe according to Embodiment 1 of the present disclosure.
Figure 2:
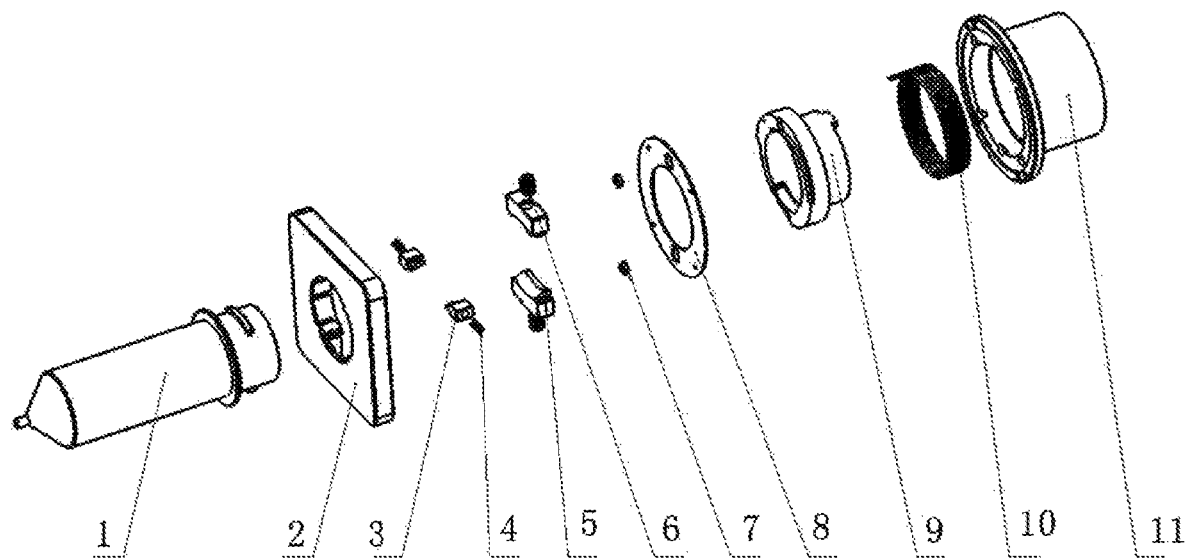
FIG. 2 is a schematic exploded diagram of the device for rapidly loading and releasing the syringe according to Embodiment 1 of the present disclosure.

The following describes in detail the present disclosure with reference the accompany drawings of embodiments of the present disclosure. However, the present disclosure may be implemented in multiple different forms, which should not be limited by the embodiments. On the contrary, the embodiments are provided to implement the full and complete disclosure, and to enable a person skilled in the art to fully understand the scope of the present disclosure. In the accompanying drawings, for clarity, sizes and relative sizes of layers and areas may be enlarged.

It should be noted that all direction indications (for example, up, down, left, right, front, and back) in the embodiments of the present disclosure are merely used to explain a relative location relationship between components and moving statuses of the components in a particular gesture (as shown in the accompanying drawings), and if the particular gesture changes, the direction indications change correspondingly.

The present disclosure provides a syringe and a device for rapidly loading and releasing the syringe. The device is mounted onto a injector, to rapidly loading and releasing the syringe, between the syringe and the rejector or between the syringe and another component.

A limiting flange and a clamping flange are disposed on an outer side wall of a connection end of the syringe, the clamping flange is approximate to a rear end of the connection end of the syringe, and the clamping flange includes at least two clamping portions that are disposed on the same circle.

The device for rapidly loading and releasing the syringe includes an injection head, at least two bayonet locks, a pushing ring, and a guide sleeve, both of the bayonet locks are on the same circle, and the bayonet locks 5 are disposed on the injection head by means of first elastic structures in a manner of being flexible along a radial direction. One end of the pushing ring stretches into the guide sleeve, and a second elastic structure is disposed between the pushing ring and the guide sleeve. The other end of the pushing ring faces sides of the bayonet locks. Bump components are disposed on the sides of the bayonet locks, bump slots are disposed on locations, corresponding to the bump components, on an end surface of the other end of the pushing ring, and the bump components stretch into the bump slots. The pushing ring rotates relative to the bayonet locks, and when the bump components slide along the bump slots, the bump components drive the bayonet locks to move along a radial direction. Clamping slots used for insertion of the clamping portions are further disposed on the end surface, facing the bayonet locks, of the pushing ring.

During loading of the syringe 1, the syringe is inserted into the injection head, the clamping portions push the bayonet locks away, and the bayonet locks move outwards along a radial direction and act on the first elastic structures. After the clamping flange passes through the bayonet locks, the bayonet locks are restored under the action of the first elastic structures and abut on the outside of the syringe. A side of the clamping flange abuts on the sides of the bayonet locks, and a side of the limiting flange abuts on an outer side wall of the injection head, so that the syringe is positioned along an axial direction. Each clamping portion of the clamping flange stretches into the corresponding clamping slot.

During releasing of the syringe 1, the syringe is rotated, and drives, by means of the clamping portions inside the clamping slots, the pushing ring to rotate, and the pushing ring rotates and acts on the second elastic structure. The pushing ring rotates, so the bump components move in the bump slots to drive the bayonet locks to move outwards along a radial direction, further the bayonet locks are disengaged from the clamping flange, and the syringe is pulled out along an axial direction. After the syringe is released, under the action of the second elastic structure, the pushing ring rotates and is restored.

By means of the device for rapidly loading and releasing a syringe provided in the present disclosure, a syringe provided with a limiting flange and a clamping flange can be loaded onto and removed from the device rapidly as long as the syringe is rotated, so that an operation is convenient and a structure is simple and compact. In addition, the syringe is connected to the device stably, and does not shake easily, thereby implementing stable connection to an injector.

The following further describes specific embodiments.

Embodiment 1

Referring to FIG. 1 to FIG. 19, this embodiment provides a device for rapidly loading and releasing a syringe.

In this embodiment, a clamping flange includes two clamping portions 100, and the two the clamping portions 100 are disposed on an outer side wall of the syringe 1 symmetrically along a circumferential direction. Correspondingly, two bayonet locks 5 that are disposed symmetrically along a circumferential direction are disposed inside an injection head. Certainly, in another embodiment, there may be three, four, or five clamping portions 100, which is not limited herein.

In this embodiment, a socket is disposed on an end, connected to the syringe 1, of the injection head 2, so that the syringe is inserted into the injection head 2, the ring of the socket and the bayonet locks located, a pushing ring, and a guide sleeve are disposed based on a same axis. The bayonet locks 5 are directly disposed inside the socket, the pushing ring 9 and the guide sleeve 11 are disposed sequentially on the other end of the injection head 2, and are communicated with the socket based on the same axis.

Figure 3:
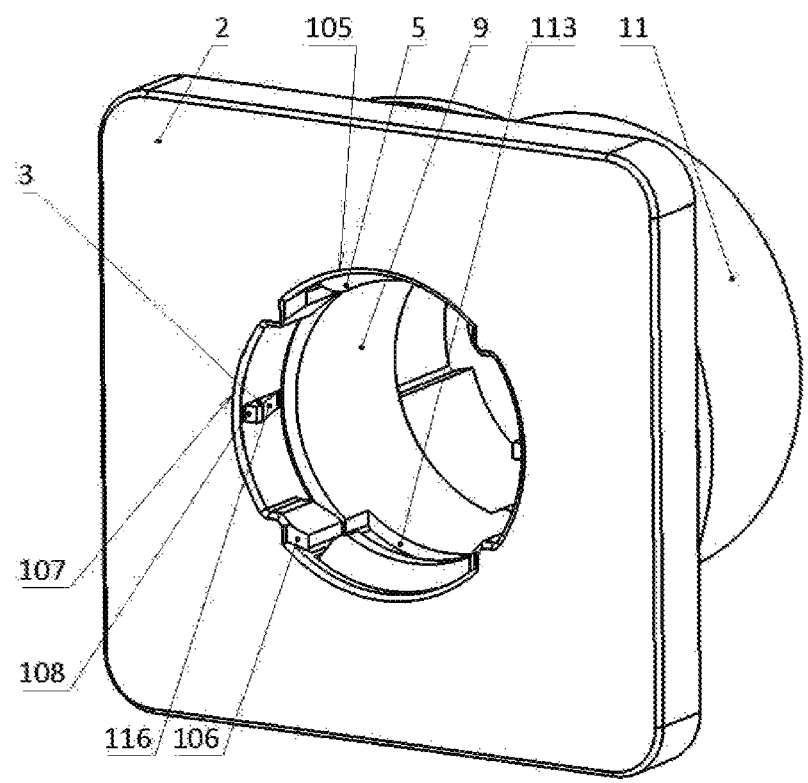
FIG. 3 is a schematic structural diagram of the device for rapidly loading and releasing the syringe according to Embodiment 1 of the present disclosure.

Referring to FIG. 3, loading slots 105 are respectively disposed on locations, corresponding to the bayonet locks, on an edge of an inside of the socket of the injection head 2, and the two loading slots 105 are disposed symmetrically along a circumferential direction. When the syringe 1 is inserted into the injection head 2, the clamping portions 100 on the outside of the syringe 1 are inserted along the loading slots 105. The loading slots 105 play a role of guiding, so that the injection head can be inserted into the injection head 2 easily.

Further, first chamfers 102 are disposed on two ends of each of the clamping portions 100, second chamfers 106 matching the first chamfers 102 are further disposed on two ends of each of the loading slots 105, and the first chamfers 102 matches the second chamfers 106, helping to insert the clamping portions 100 into the loading slots 105. In addition, chamfers are disposed on edges on sides, facing outwards, of the loading slots 105, so that edges of the clamping portions 100 can be inserted into the loading slots 105 rapidly.

Figure 4:
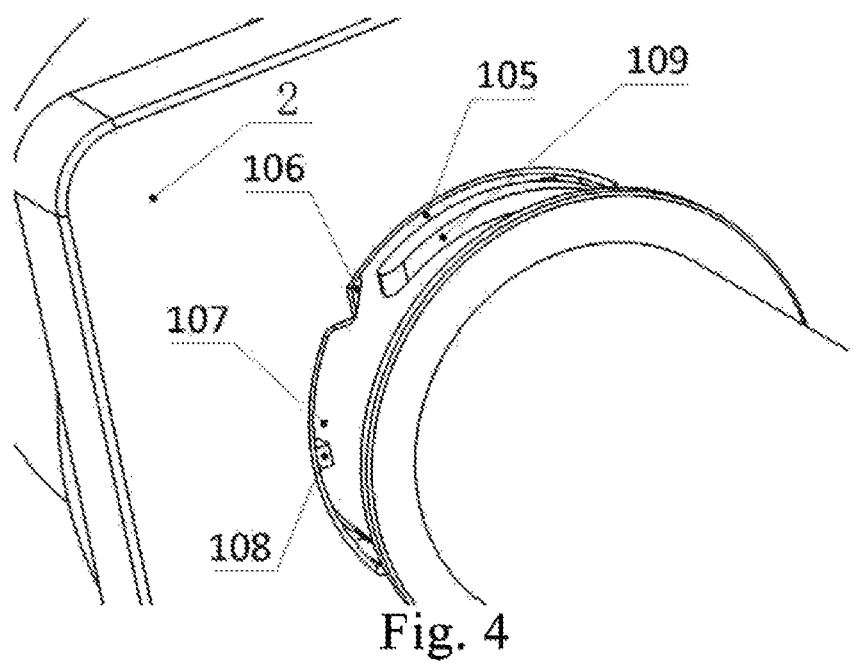
FIG. 4 is a schematic diagram showing that clamping portions are loaded from loading slots during loading of the syringe in Embodiment 1.
Figure 5:
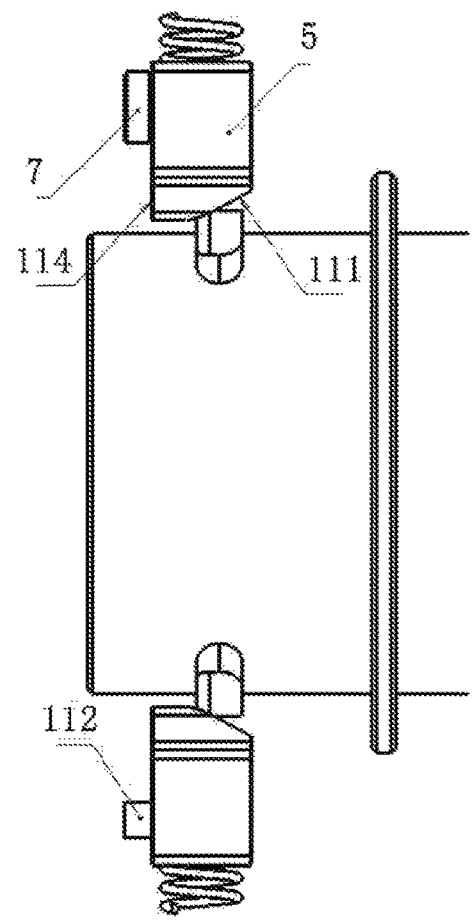
FIG. 5 is a schematic diagram showing ramps of the clamping portions abut on ramps of the two bayonet locks and push the bayonet locks away in Embodiment 1.
Figure 7:
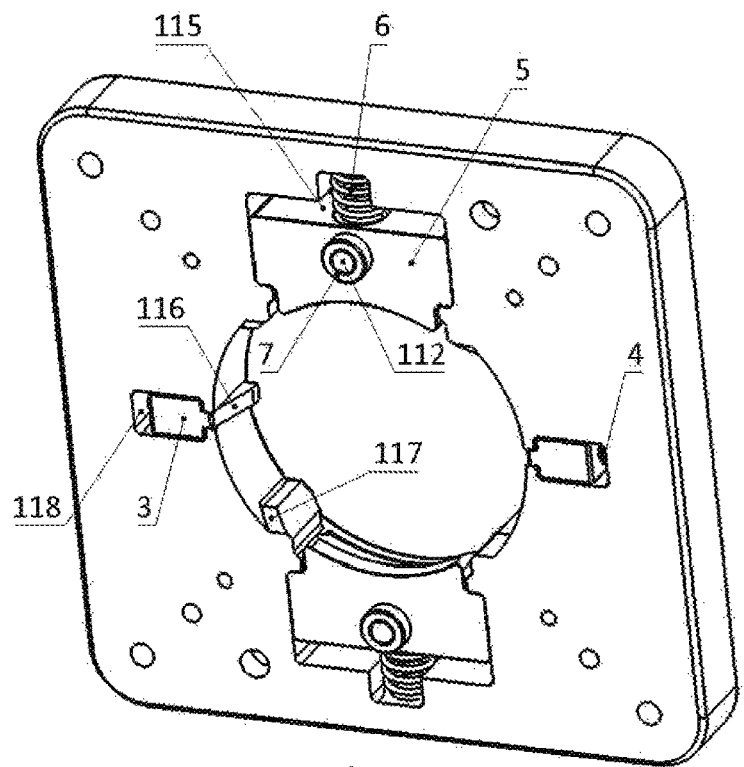
FIG. 7 is a schematic structural diagram of the back of the injection head, bayonet locks, and backing pins in Embodiment 1.

Referring to FIG. 4 and FIG. 7, two bayonet locks 5 are respectively disposed in the two loading slots 105. Specifically, the first set of slots 115 are disposed inside the loading slots 105, one end of each of the bayonet locks 5 is inserted into one of the corresponding first set of slots 115, first elastic structures 6 are disposed between the bayonet locks 5 and the first set of slots 115, and the other end stretches out from the corresponding loading slot 105. Meanwhile, inner sides of the bayonet locks 5 are fixed onto the injection head 2 by means of stop rings 8 (shown in FIG. 2). After the clamping portions 100 stretch into the injection head 2 under the guiding action of the loading slots 105, the clamping portions 100 abut on the bayonet locks 5 and continue to exert force, and the clamping portions 100 separate the bayonet locks 5, so that the bayonet locks 5 abut on the first elastic structures 6, and move outwards along the first set of slots 115 along a radial direction. The first set of slots 115 is disposed to stop the bayonet locks 5 and limit sliding directions of the bayonet locks.

Further, the first elastic structures 6 are implemented by using springs, and certainly, may be flat springs in another embodiment, which is not limited herein.

Further, sides (that is, sides facing the injection head 2 during loading), away from the limiting flange 103, of the clamping portions 100 are first ramps 101, and second ramps 111 matching the first ramps 101 are disposed on end surfaces (that is, sides facing the clamping portions 100 during loading) of the bayonet locks 5. In the present disclosure, the first ramps 101 and the second ramps 111 are disposed, so that the bayonet locks 5 can be separated successfully, and the clamping portions 100 pass through the bayonet locks 5.

In this embodiment, the bayonet locks 5 are directly disposed inside the loading slots 105 of the socket, so that the structure is compact. Certainly, in another embodiment, the bayonet locks may not be disposed inside the loading slots 105, as long as it is ensured that locations of the loading slots correspond to locations of the bayonet locks 5, that is, it is ensured that under the guiding action of the loading slots, the clamping portions abut on the bayonet locks 5 and separate the bayonet locks, which is not limited herein.

In this embodiment, the pushing ring 9 is disposed inside the guide sleeve 11 based on a same axis, the guide sleeve 11 is connected to the other end of the injection head 2, and the connection may be implemented by using a screw or the like, which is not limited herein. Bump components disposed on the sides of the bayonet locks 5 pass through the stop rings 8 and then stretch into and cooperate with bump slots 119 on an end surface of the pushing ring 9.

Figure 6:
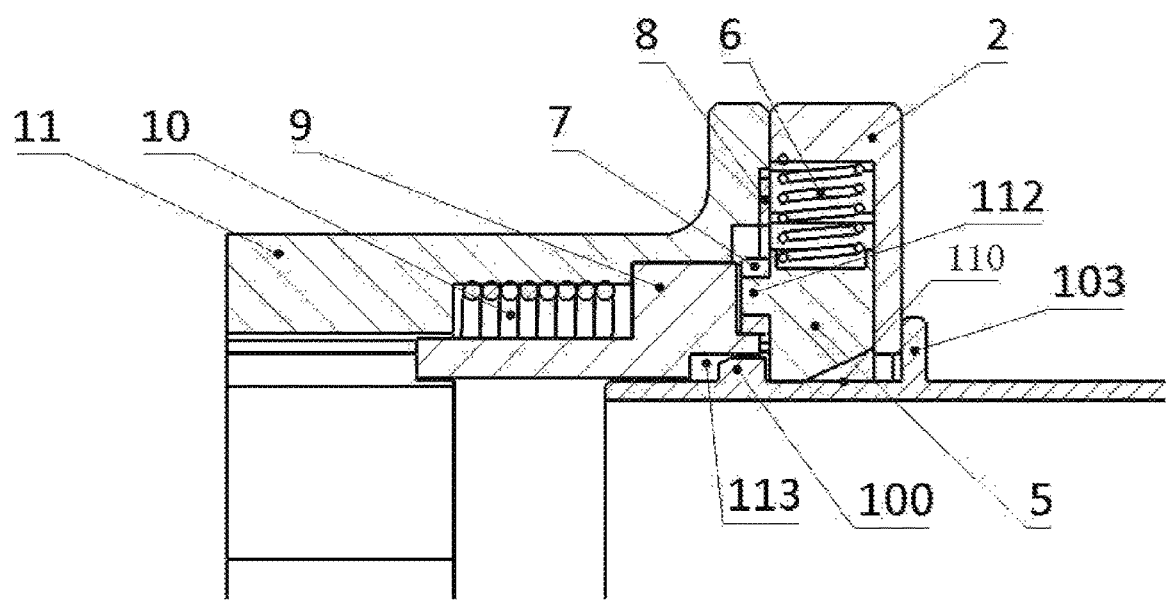
FIG. 6 is a schematic diagram after the syringe is loaded completely in Embodiment 1.

Further, referring to FIG. 6, clamping slots 113 are disposed on the end surface, facing the injection head 2, of the pushing ring 9, the clamping slots 113, the loading slots 105, and the bayonet locks 5 are in a same straight line, and sizes and shapes of the clamping slots 113 match those of the clamping portions 100, so that after the clamping portions 100 pass through the bayonet locks 5 and are loaded, the clamping portions 100 stretch into the clamping slots 113, and when the syringe is rotated, the syringe may drive the pushing ring 9 to rotate together.

Further, referring to FIG. 7, the bump components include embossed bearing shafts 112 disposed on the sides of the bayonet locks 5 and bearings 7 sleeved on the embossed bearing shafts 112. In the present disclosure, the bearings 7 are disposed, so that the bump components slide inside the bump slots 119, and frictional resistance is reduced, facilitating rapid releasing of the syringe. Certainly, in another embodiment, structural forms of the bump components are not limited thereto, and the bump components may be implemented by using rollers, which is not limited herein.

Figure 8:
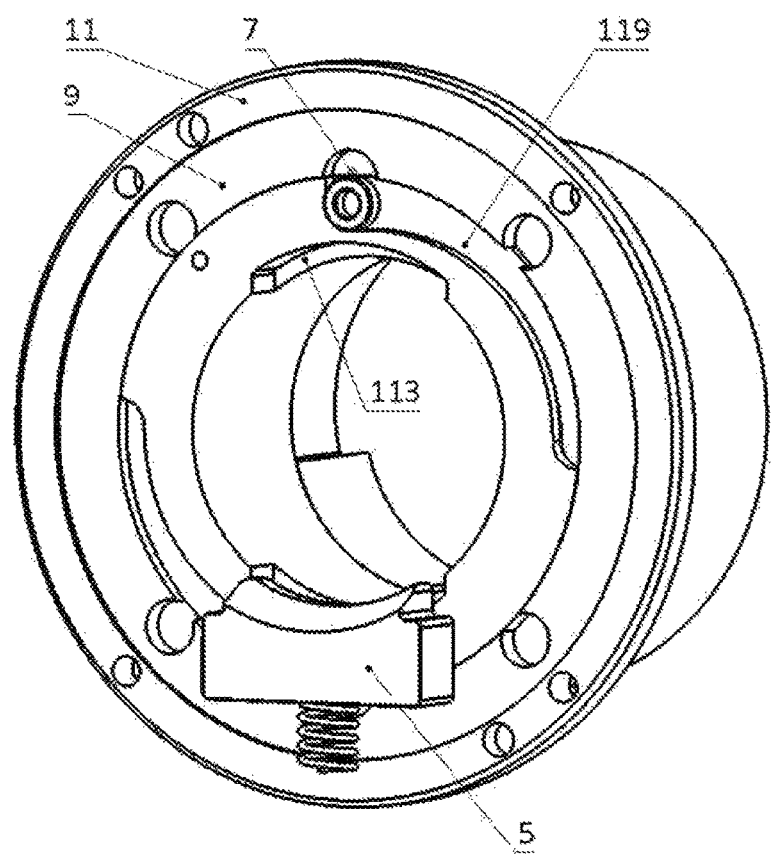
FIG. 8 is a schematic diagram showing location statuses of the bayonet locks, bearings, and the pushing ring, a relative location relationship between the bearings and slots on the pushing ring, and a relative location relationship between the bayonet locks and the slots on the pushing ring before the syringe is loaded in Embodiment 1.
Figure 9:
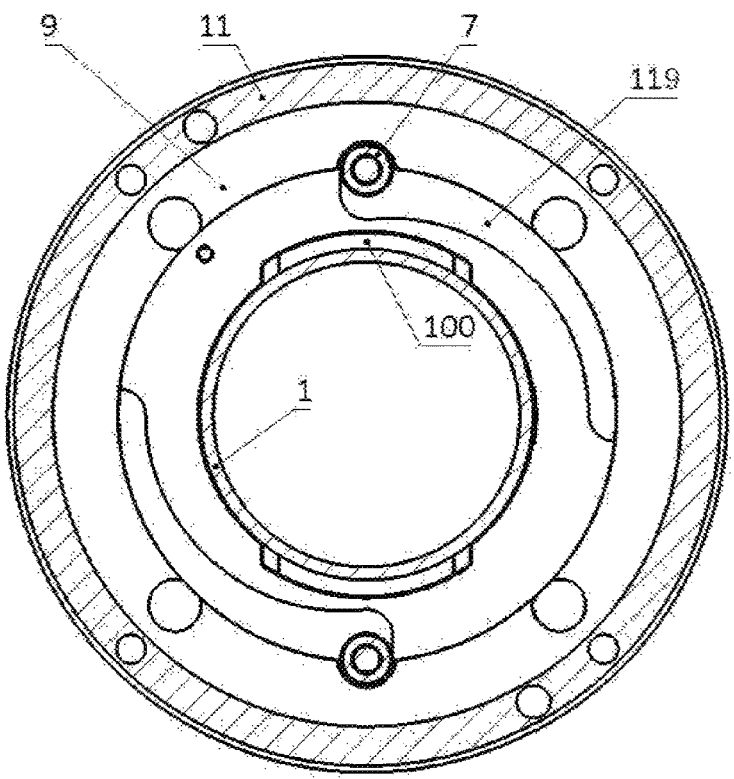
FIG. 9 is a schematic diagram showing location statuses of two bearings and the pushing ring and a relative location relationship between the two bearings and two slots on the pushing ring when two clamping portions push the two bayonet locks away to the maximum during loading of the syringe in Embodiment 1.
Figure 10:
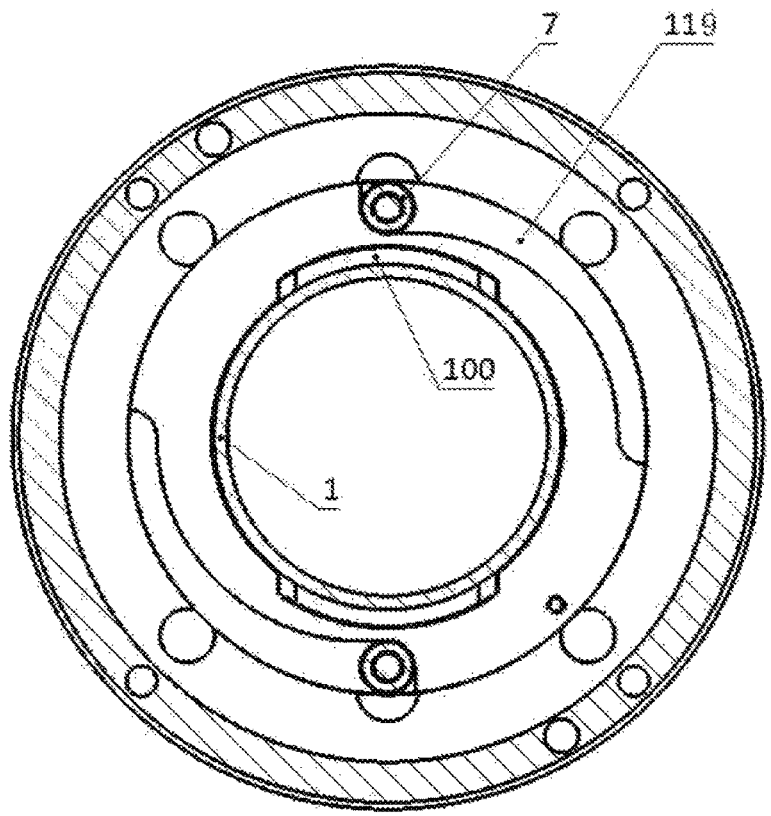
FIG. 10 is a schematic diagram showing location statuses of two bearings and the pushing ring and a relative location relationship between the two bearings and two slots on the pushing ring after the syringe is loaded completely in Embodiment 1.
Figure 11:
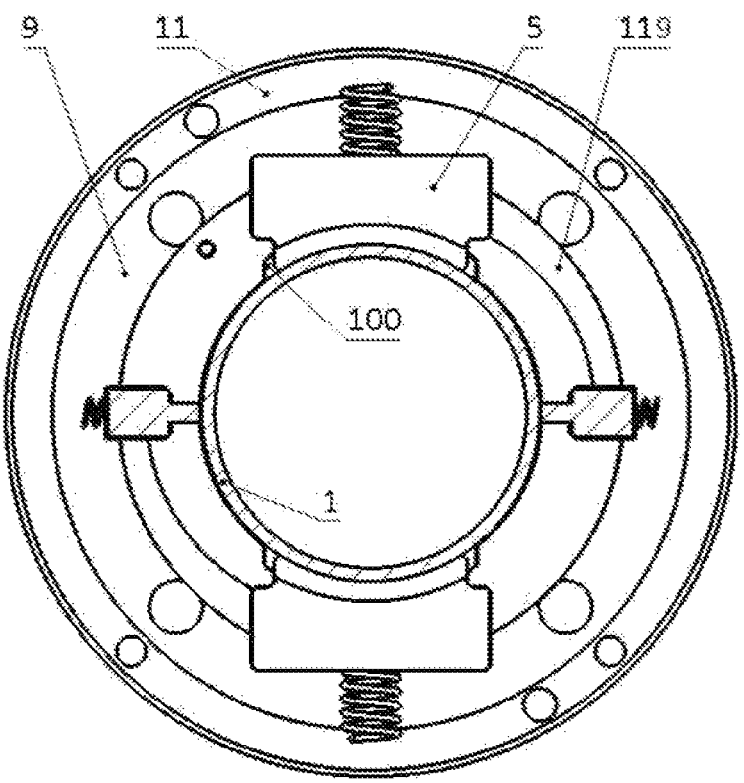
FIG. 11 is a schematic diagram showing location statuses of the syringe, two bayonet locks, and two backing pins after the syringe is loaded completely in Embodiment 1.
Figure 12:
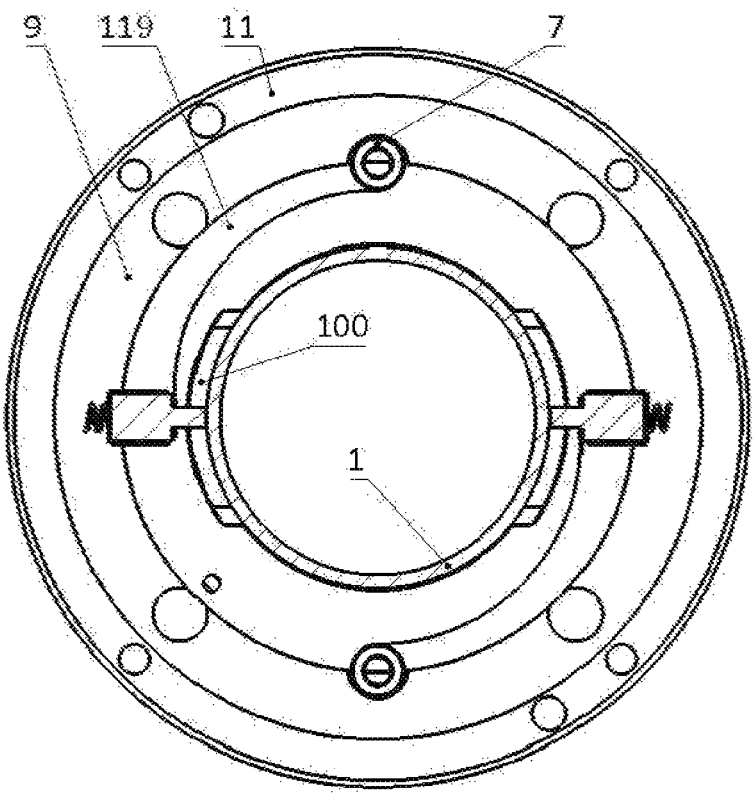
FIG. 12 is a schematic diagram showing location statuses of the syringe, two bearings, and two backing pins and a relative location relationship between the two bearings and two slots on the pushing ring after the syringe is rotated counterclockwise by 90 degrees during releasing of the syringe in Embodiment 1.
Figure 13:
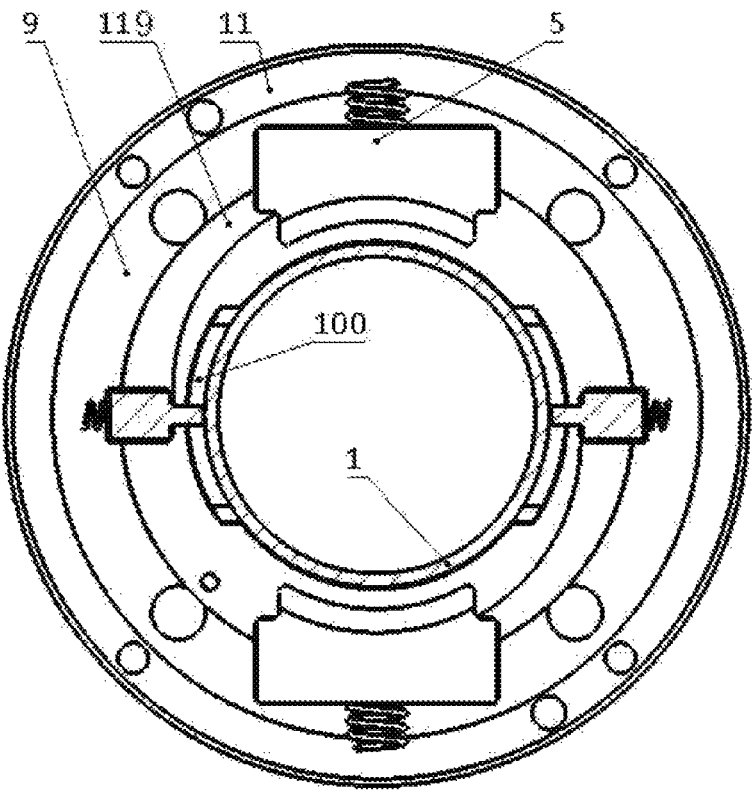
FIG. 13 is a schematic diagram showing a relative location relationship between two bayonet locks and the syringe after the syringe is rotated counterclockwise by 90 degrees during releasing of the syringe in Embodiment 1.
Figure 14:
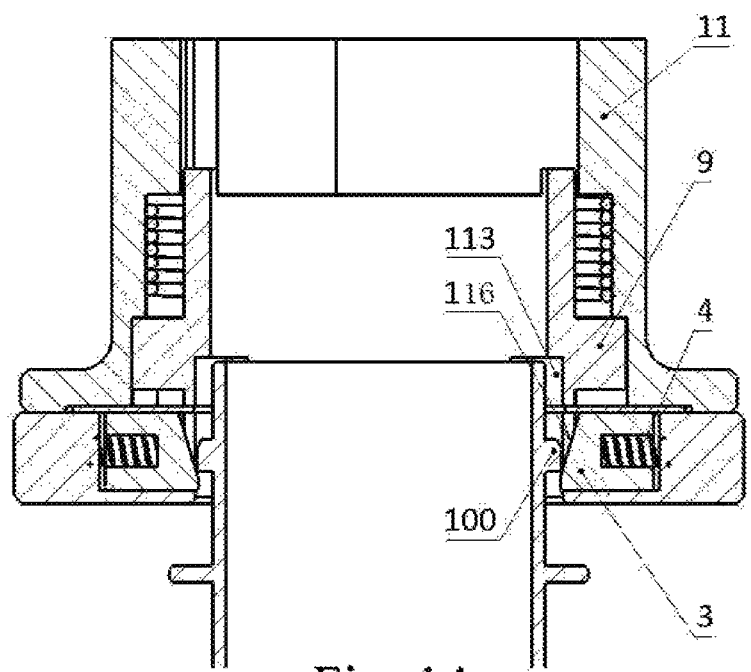
FIG. 14 is a schematic diagram showing that the two clamping portions abut on backing pin ramps of two backing pins and push to separate the two backing pins during releasing of the syringe in Embodiment 1.

Further, referring to FIG. 8 to FIG. 10, the bump slots 119 are disposed along a circumferential direction, and each bump slot gradually deviates from the center from an initial end to a tail end, that is, an internal circle of each bump slot 119 approaches an external circle gradually, so that a width is reduced gradually. In the present disclosure, by means of the structures of the bump slots, when the pushing ring 9 rotates relative to the bayonet locks 5, the bump slots 119 move relative to the bump components, so that the internal peripheries of the bump slots gradually move outwards along a radical direction to push the bump components, and the bump components drive the bayonet locks to move outwards along a radial direction.

Figure 15:
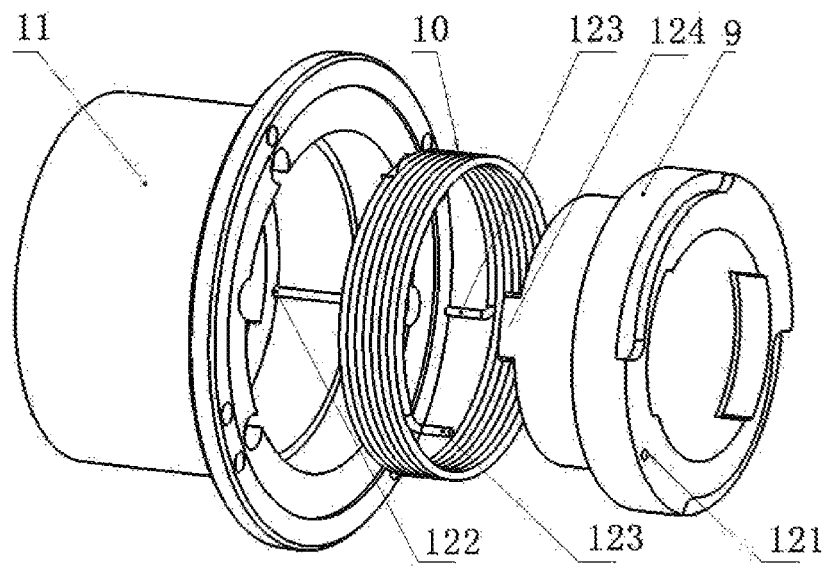
FIG. 15 is a schematic diagram showing a manner of installing the torsion spring on the pushing ring and the guide sleeve in Embodiment 1.
Figure 16:
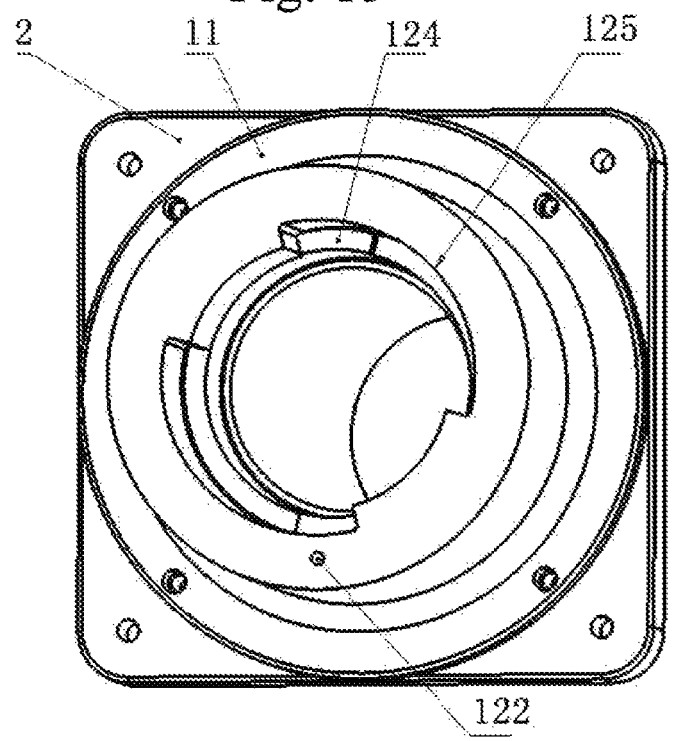
FIG. 16 is a schematic diagram showing initial locations of two limiting bosses on the pushing ring inside two limiting slots on the guide sleeve in Embodiment 1.
Figure 17:
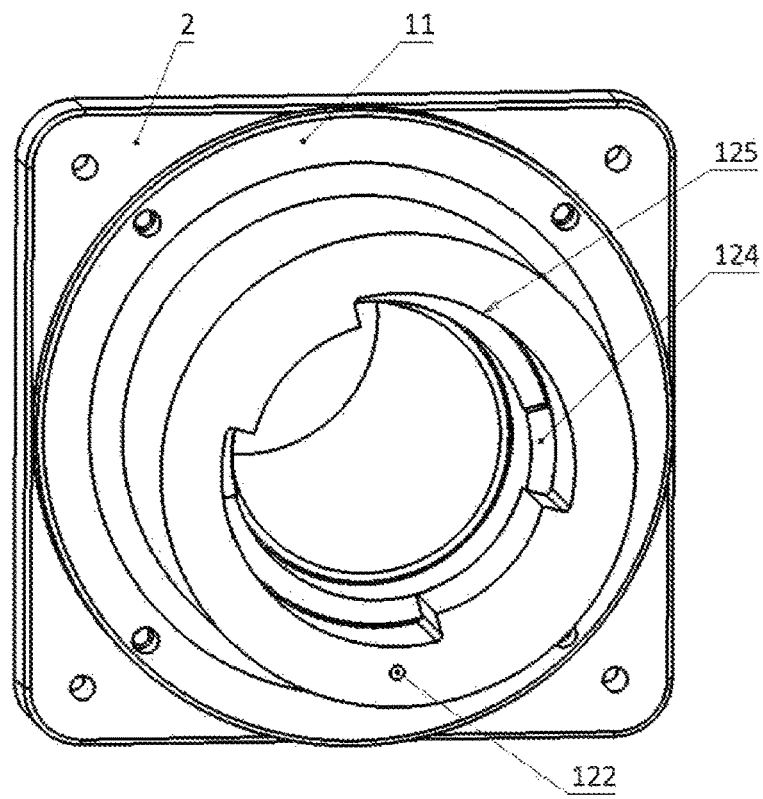
FIG. 17 is a schematic diagram showing locations of the two limiting bosses on the pushing ring inside the two limiting slots on the guide sleeve after the pushing ring rotates by 90 degrees in Embodiment 1.
Figure 18:
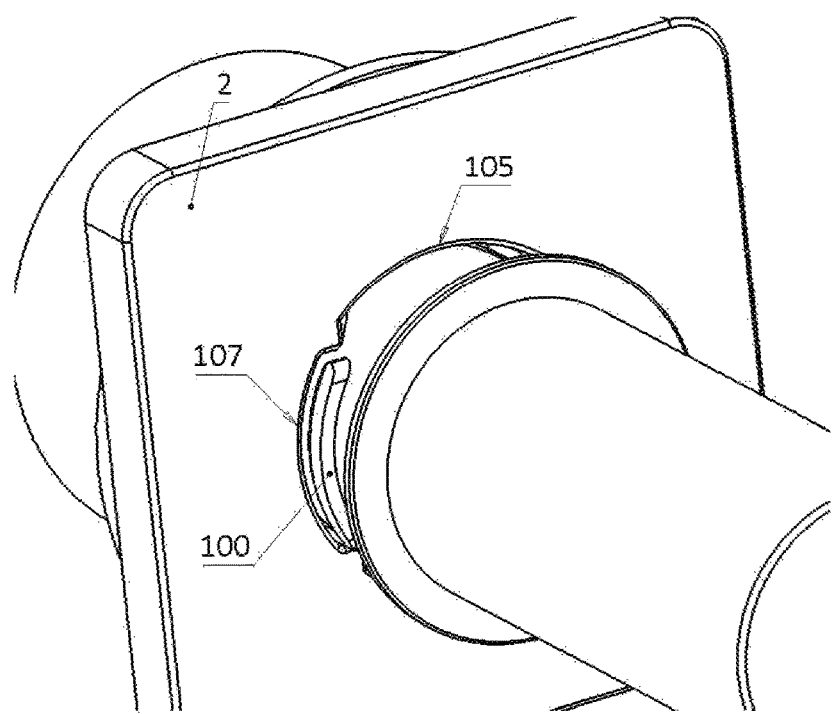
FIG. 18 is a schematic diagram showing that the two clamping portions of the syringe exit along two releasing slots on the injection head in Embodiment 1.
Figure 19:
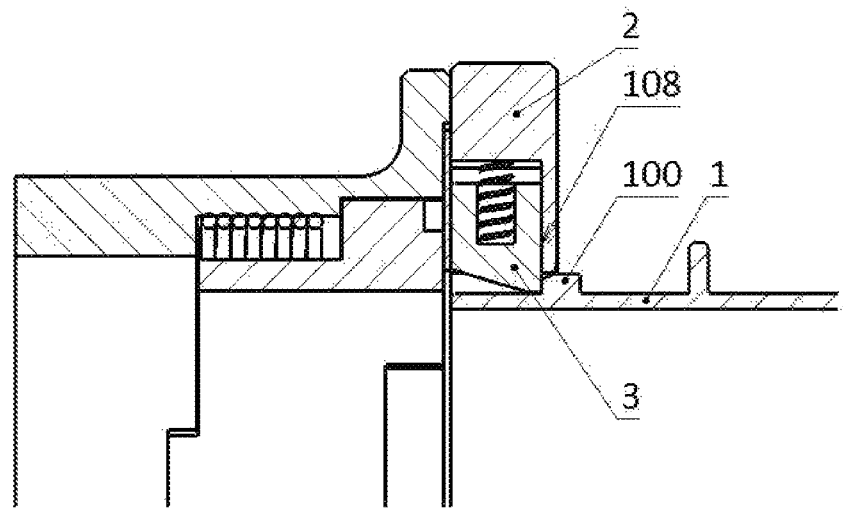
FIG. 19 is a schematic diagram showing that the two clamping portions of the syringe exit along two releasing slots on the injection head and two backing pins prevent further insertion of two clamping flanges in Embodiment 1.
Figure 20:
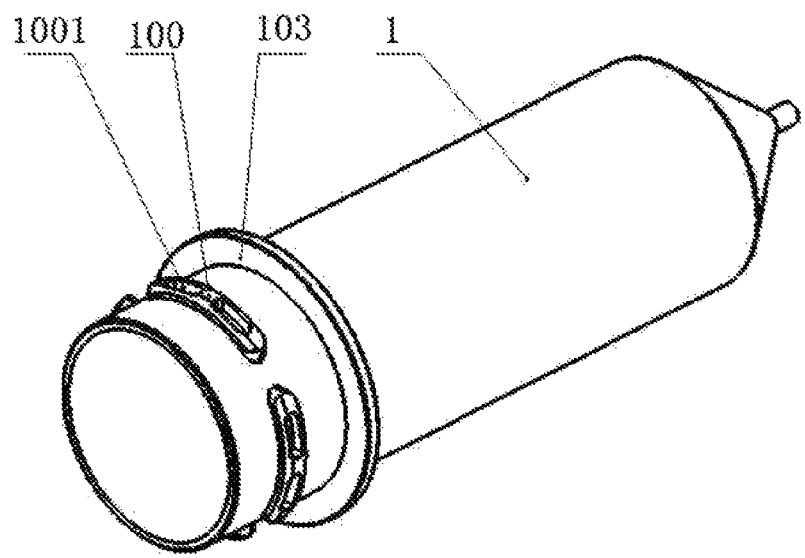
FIG. 20 is a schematic structural diagram of a syringe in Embodiment 2.
Figure 21:
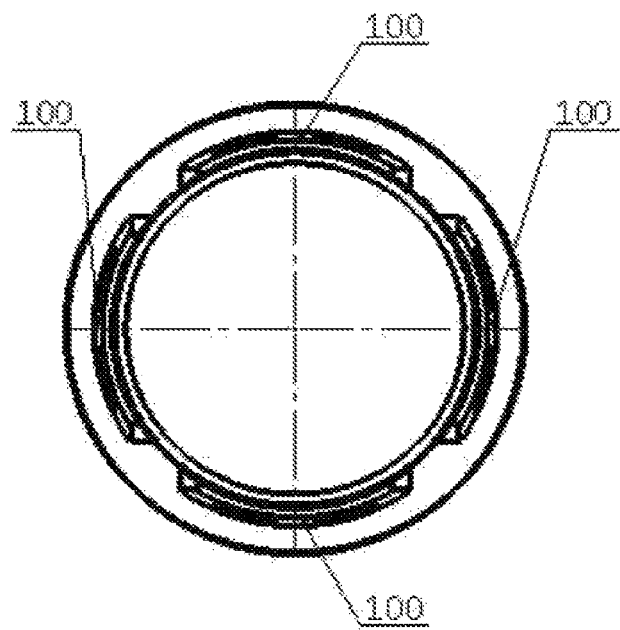
FIG. 21 is a schematic diagram showing locations of four clamping portions on the syringe in Embodiment 2.

In this embodiment, referring to FIG. 15, FIG. 16, and FIG. 17, limiting bosses 124 are disposed on an end, stretching into the guide sleeve 11, of the pushing ring 9, guide sleeve limiting slots 125 are disposed inside the guide sleeve 11, the limiting bosses 124 stretch into the guide sleeve limiting slots 125, the pushing ring 9 rotates relative to the guide sleeve, and the limiting bosses 124 slides along the guide sleeve limiting slots 125, to limit a range of an angle by which the pushing ring rotates. In this embodiment, because only two clamping portions 100 are disposed, the pushing ring needs to rotate only by 90 degrees, and the guide sleeve limiting slots 125 occupy a quarter of the entire ring in this application, to limit a rotation angle of the pushing ring to 90 degrees. Certainly, in another embodiment, if a quantity of the clamping portions changes, the rotation angle changes correspondingly, which is not limited herein.

In this embodiment, referring to FIG. 15, the second elastic structure 10 is a torsion spring, the torsion spring is sleeved on an external circle of the pushing ring 9, one end of the torsion spring is fixed onto the pushing ring 9, and the other end is fixed onto the guide sleeve 11. Specifically, a torsion spring socket 121 is disposed on the pushing ring 9, and one support leg 123 of the torsion spring is connected and fixed into the torsion spring socket 121. Another torsion spring socket 122 is disposed on an inside of the guide sleeve 11, and the other support leg of the torsion spring is connected and fixed into the torsion spring socket 122. When the pushing ring 9 rotates relative to the guide sleeve 11, the torsion spring deforms, to generate resilience force to restore the pushing ring 9. Certainly, in another embodiment, the second elastic structure 10 may be implemented by using a flat spring, which is not limited herein.

In this embodiment, two releasing slots 107 are further disposed inside the socket on the injection head 2. The releasing slots 107 are disposed, so that the two clamping portions 100 exit from the releasing slots 107 during releasing of the syringe. The releasing slots 107 are disposed symmetrically along a circumferential direction, and the releasing slots 107 and the loading slots 105 are arranged in an alternate manner and are on the same circle.

In this embodiment, backing pins 3 are respectively disposed inside the two releasing slots 107. In the present disclosure, the backing pins 3 are disposed, so that the clamping portions are prevented from stretching into the releasing slots 107 during loading of the syringe, thereby avoiding a misoperation.

Specifically, referring to FIG. 4 and FIG. 7, the second set of slots 118 are disposed inside the releasing slots 107, one end of each of the backing pins 3 stretches into one of the corresponding second set of slots 118, third elastic structures 4 are disposed between the backing pins 3 and the second set of slots 118, and the other end stretches out from the one of the corresponding second set of slots 118. Further, sides, facing the pushing ring, of ends of the backing pins 3 stretching out from the second set of slots 118 are of a ramp shape, that is, form backing pin ramps 116. The backing pin ramps 116 are disposed, so that the clamping portions 100 successfully separate the backing pins 3 during exiting.

During loading, because the backing pins 3 are disposed, the clamping portions cannot be inserted into the releasing slots 107, and can be inserted only from the loading slots 105. During releasing, the syringe is rotated by 90 degrees, the clamping portions on the syringe are exactly opposite to the releasing slots 107, and the syringe is pulled out along an axial direction, abuts on the backing pin ramps 116, and pushes the two backing pins 3 to separately move left and right, so that the clamping portions exit successfully. The two backing pins 3 move outwards along a radial direction and compress or stretch the third elastic structures 4, the third elastic structures 4 generate resilience force, and after releasing is completed, the backing pins 3 are restored under the action of the third elastic structures.

In this embodiment, quantities of the bayonet locks 5, the backing pins 3, the releasing slots, and the loading slots correspond to the quantity of the clamping portions, which is not limited herein. The following further describes a working principle of the device for rapidly loading and releasing a syringe provided in this embodiment. Specific details are as follows:

1. Loading Process

Referring to FIG. 4 to FIG. 11, the syringe 1 is inserted into the injection head 2, and under the guiding action of the loading slots 105, the clamping portions 100 are inserted along corresponding loading slots 105 (it should be noted that, if the clamping portions 100 on the syringe are inserted towards the releasing slots 107, the outsides 108 of the backing pins 3 abut on the clamping portions, and stop further insertion of the clamping portions 100, this may avoid a misoperation). An end surface 104 of the connection end of the syringe does not abut on the backing pins 3. The clamping portions 100 first abut on the bayonet locks 5, and exert force along an axial direction of the syringe. The first ramps 101 of the clamping portions 100 abut on the second ramps 111 of the bayonet locks 5, the clamping portions 100 push to enable the bayonet locks 5 to move outwards along a radial direction, and the bayonet locks compress the first elastic structures 6 to generate resilience force.

The syringe continues to be inserted. When a side, facing the clamping flange, of the limiting flange 103 abuts on an external end surface of the injection head, the syringe 1 cannot continue to be inserted, and the clamping portions 100 are disengaged from the bayonet locks 5. In this case, sides 109, facing the limiting flange 103, of the clamping portions abut on sides 114 of the bayonet locks 5, thereby the syringe is limited along an axial direction. At the same time, after the clamping portions 100 are disengaged from the bayonet locks 5, under the action of resilience force of the first elastic structures, the bayonet locks 5 are restored and abut on the outside 110 of the syringe, to lock the syringe 1, so as to ensure stability of the syringe after loading, thereby preventing the syringe from shaking. Then, loading is completed.

In this case, the clamping portions 100 are located inside the corresponding clamping slots 113 on the pushing ring.

2. Releasing Process

Referring to FIG. 12 to FIG. 19, the syringe is rotated counterclockwise, and the syringe is clocked inside the clamping slots 113 by means of the clamping portions, to drive the pushing ring 9 to rotate. Because the pushing ring 9 rotates relative to the guide sleeve, under the cooperated action of the limiting bosses 124 and the guide sleeve limiting slots 125, the pushing ring 9 rotates by 90 degrees. The pushing ring 9 rotates to drive the second elastic structure 10 to twist to generate resilience torque. During rotation of the pushing ring 9, by means of special shapes of the bump components and the bump slots, the bump components move outwards along a radial direction, to push the bayonet locks 5 to move outwards along a radial direction. The two bayonet locks 5 move outwards, and no longer hold the outside 110 of the syringe. In this case, the clamping portions 100 rotate to the releasing slots 107, and under the guiding action of the chamfers 117 on the releasing slots 107 and the chamfers 102 on the clamping portions 100, the syringe easily moves outwards along an axial direction.

When the syringe moves outwards along an axial direction, the clamping portions 100 abut on the backing pin ramps 116 of the backing pins 3, to push the two backing pins 3 to move outwards along a radial direction. When the backing pins 3 move outwards, the third elastic structures 4 are compressed to generate resilience force. Under the action of the resilience force, the syringe is rapidly released, until the syringe is completely disengaged from the injection head 2, to complete an entire release process.

After the syringe is released, the backing pins 3 are restored under the action of the third elastic structures 4, the pushing ring 9 is restored under the action of the second elastic structure 10, and the bayonet locks 5 are restored under the action of the first elastic structures 6.

Embodiment 2

Referring to FIG. 20 to FIG. 24, this embodiment provides a device for rapidly loading and releasing a syringe. This embodiment is a modification made based on Embodiment 1.

Specifically, in this embodiment, four clamping portions 100 that are disposed on the same circle are disposed on an outer side wall of the syringe. The four clamping portions 100 are evenly arranged along a circumferential direction, and correspondingly, four loading slots 105 that are arranged along an axial direction on a circle of a socket of the injection head 2. The slots may be used as the loading slots and releasing slots. One pin 5 is disposed inside each of the two symmetric loading slots 105 (shown in FIG. 4), and no backing pin is disposed on the other two symmetric loading slots 105. Correspondingly, four clamping slots 113 are evenly arranged on the pushing ring 9 along a circumferential direction, and the clamping slots 113 are in one-to-one correspondence with the loading slots 105.

For another structural form of the device for rapidly loading and releasing a syringe provided in this embodiment, refer to descriptions in Embodiment 1, and details are not described herein again.

The following further describes a working principle of the device for rapidly loading and releasing a syringe provided in this embodiment. Specific details are as follows.

1. Loading Process

Figure 22:
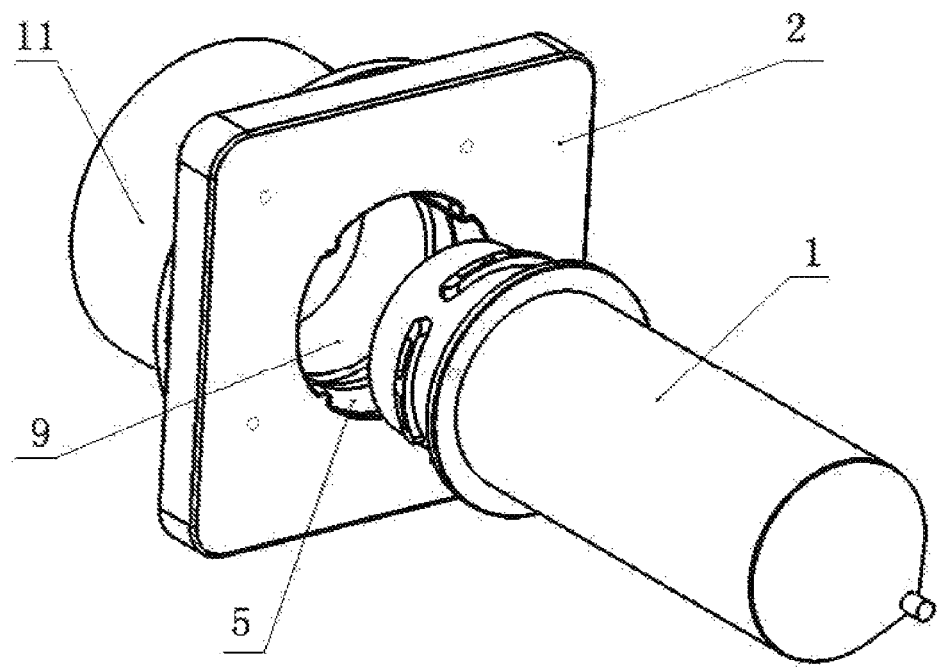
FIG. 22 is a schematic diagram showing corresponding locations of four clamping flanges and four loading/releasing slots on a loading head end during loading and releasing of the syringe in Embodiment 2.
Figure 23:
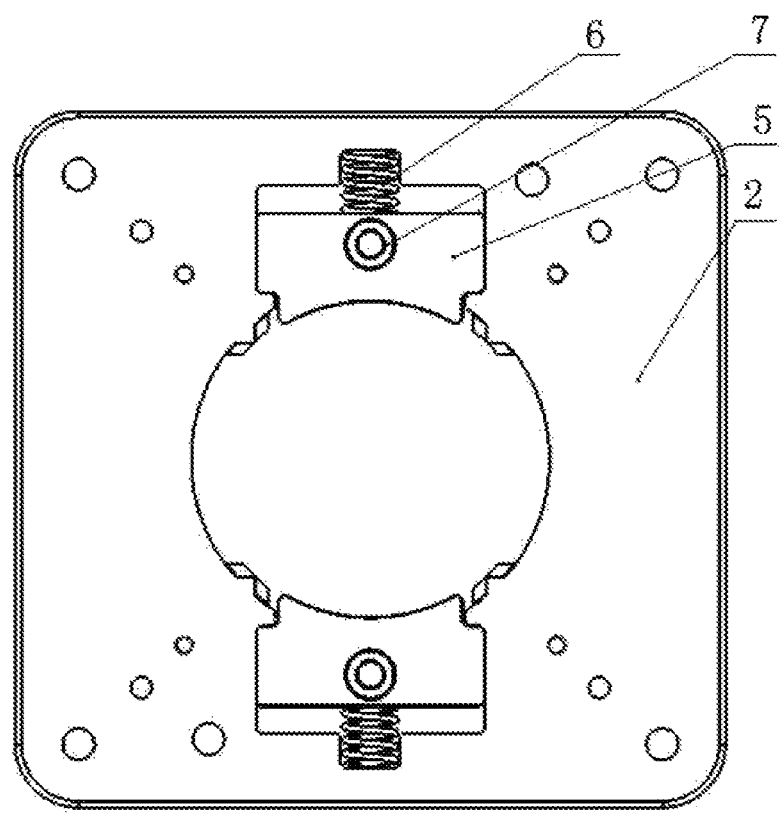
FIG. 23 is a schematic back diagram of the injection head in Embodiment 2.
Figure 24:
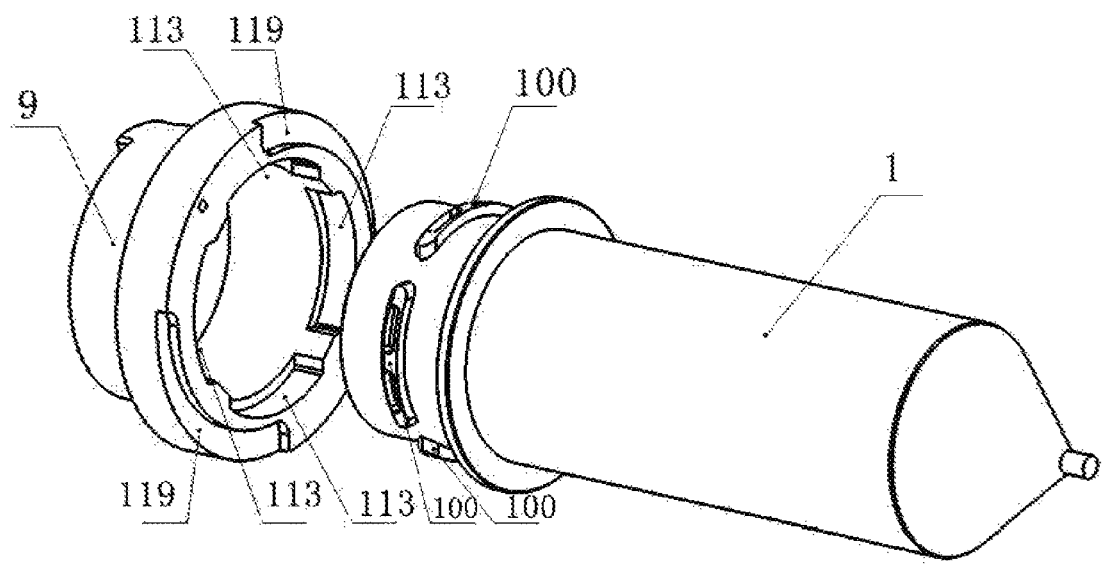
FIG. 24 is a schematic diagram showing corresponding locations of the four clamping portions on the syringe and clamping slots on the pushing ring in Embodiment 2.

As shown in FIG. 22, the four clamping portions 100 are inserted along the four loading slots 105 on the injection head 2. Two opposite clamping portions 100 abut on the two bayonet locks 5, and push the bayonet locks 5 to move outwards along a radial direction. In this process, the bayonet locks 5 compress the first elastic structures 6 and enable the first elastic structures to generate resilience force.

When the limiting flange 103 abuts on the injection head 2, the syringe 1 cannot be inserted further. The two opposite clamping portions 100 are disengaged from the bayonet locks 5, and the sides of the clamping portions 100 abut on the sides of the backing pins to implement limiting along an axial direction. In this process, the other two clamping portions 100 directly pass through the other two loading slots 105. Meanwhile, after the bayonet locks 5 are disengaged from the clamping portions 100, under the action of the resilience force of the first elastic structures 6, the bayonet locks 5 are restored and tightly hold the outside of the syringe, to complete loading of the syringe.

In this case, the four clamping portions 100 respectively stretch into the four clamping slots 113 on the pushing ring 9.

2. Releasing Process

The syringe 1 is rotated. Because the clamping portions 100 on the syringe 1 are located inside the clamping slots 113 on the pushing ring 9, the pushing ring 9 rotates counterclockwise by 90 degrees together with the syringe 1.

During rotation of the pushing ring 9, the second elastic structure generates resilience torque. The pushing ring rotates, and pushes to enable, by means of cooperation between the bump slots and the bump components, the two bayonet locks to move outwards along a radial direction, so that the bayonet locks 5 are disengaged from the clamping portions 100. In this case, the four clamping flange 100 still correspond to the four loading slots 105 on the injection head 2, and the syringe 1 can be pulled out, to complete releasing.

After the syringe 1 is pulled out, the pushing ring 9 is restored under the action of the resilience torque of the second elastic structure, and the bayonet locks 5 are restored under the action of the first elastic structures 6.

It should be noted that the four clamping portions 100 on the syringe 1 correspond to the four loading slots on the injection head 2 and to the four clamping slots 113 on the pushing ring 9, so that no misoperation exists. Therefore, when no backing pin is disposed, normal working of the device is not affected, a structure of the entire device is more compact, and operation is more convenient.

Embodiment 3

The present disclosure further provides a syringe. A limiting flange and a clamping flange are disposed on an outer side wall of a connection end of the syringe, the clamping flange is approximate to a rear end of the connection end of the syringe, and the clamping flange includes at least two clamping portions that are disposed on the same circle.

The syringe is connected to an injector or another component by means of a rapid loading and releasing device. The rapid loading and releasing device is directly installed onto the injector. The syringe is loaded onto or released from the device by means of the limiting flange and the clamping flange.

The device further includes an injection head, at least two bayonet locks, a pushing ring, and a guide sleeve. Both of the bayonet locks are on the same circle. The bayonet locks are disposed on the injection head by means of the first elastic structures in a manner of being flexible along a radial direction. One end of the pushing ring stretches into the guide sleeve, a second elastic structure is disposed between the pushing ring and the guide sleeve, and the other end of the pushing ring faces sides of the bayonet locks. Bump components are disposed on the sides of the bayonet locks, bump slots are disposed on locations, corresponding to the bump components, on an end surface of the other end of the pushing ring, the bump components stretch into the bump slots, the pushing ring may rotate relative to the bayonet locks, and when the bump components slide along the bump slots, the bump components drive the bayonet locks to move outwards along a radial direction. Clamping slots used for insertion of the clamping portions are further disposed on the end surface, facing the bayonet locks, of the pushing ring.

During loading, the syringe is inserted into the injection head, the clamping portions push the bayonet locks away, and the bayonet locks move outwards along a radial direction and act on the first elastic structures. After the clamping flange passes through the bayonet locks, under the action of the first elastic structures, the bayonet locks are restored and abut on the outside of the syringe. A side of the clamping flange abuts on the sides of the bayonet locks, a side of the limiting flange abuts on an outer side wall of the injection head, and the syringe is positioned along an axial direction. The clamping portions of the clamping flange respectively stretch into the clamping slots.

During releasing, the syringe is rotated, and drives, by means of the clamping portions located inside the clamping slots, the pushing ring to rotate, and the pushing ring rotates and acts on the second elastic structure. The pushing ring rotates, the bump components move inside the bump slots to drive the bayonet locks move outwards along a radial direction, the bayonet locks are disengaged from the clamping flange, and the syringe is pulled out along an axial direction. After the syringe is released, under the action of the second elastic structure, the pushing ring rotates and is restored.

In this embodiment, sides, facing away from the limiting flange, of the clamping portions are ramps.

In this embodiment, first chamfers are disposed on two ends, away from the limiting flange, of the clamping portions.

In this embodiment, the clamping flange may include two clamping portions or four clamping portions, which is not limited herein.

A person skilled in the art should understand that the present disclosure may be implemented in many other specific forms without departing from the spirit or scope thereof. Although embodiments of the present disclosure have been described, it should be understood that the present disclosure is not limited to these embodiments. A person skilled in the art may make changes and modifications within the spirit and scope of the present disclosure that are defined in the claims.

The invention claimed is:

1. A device for rapidly loading and releasing a syringe, wherein a limiting flange and a clamping flange are disposed on an outer side wall of a connection end of the syringe, the clamping flange is approximate to a rear end of the connection end of the syringe, and the clamping flange comprises at least two clamping portions that are disposed on a same circle, the device comprises an injection head, at least two bayonet locks, a pushing ring, and a guide sleeve, both of the at least two bayonet locks are on a same circle, and the at least two bayonet locks are disposed on the injection head by means of first elastic structures in a manner of being flexible along a radial direction; one end of the pushing ring stretches into the guide sleeve, and a second elastic structure is disposed between the pushing ring and the guide sleeve; an other end of the pushing ring faces sides of the at least two bayonet locks, bump components are disposed on the sides of the at least two bayonet locks, bump slots are disposed on locations corresponding to the bump components, on an end surface of the other end of the pushing ring, the bump components stretch into the bump slots, the pushing ring rotates relative to the at least two bayonet locks, and when the bump components slide along the bump slots, the bump components drive the at least two bayonet locks to move along a radial direction; clamping slots used for insertion of the at least two clamping portions are further disposed on an end surface, facing the at least two bayonet locks, of the pushing ring;

during loading, the syringe is inserted into the injection head, the at least two clamping portions push the at least two bayonet locks away, and the at least two bayonet locks move outwards along the radial direction and act on the first elastic structures; after the clamping flange passes through the at least two bayonet locks, the at least two bayonet locks are restored under the action of the first elastic structures and abut on an outside of the syringe; a side of the clamping flange abuts on the sides of the at least two bayonet locks, and a side of the limiting flange abuts on an outer side wall of the injection head, so that the syringe is positioned along an axial direction; each clamping portion of the clamping flange stretches into the corresponding clamping slot; and during releasing, the syringe is rotated, and drives, by means of the at least two clamping portions inside the clamping slots, the pushing ring to rotate, and the pushing ring rotates and acts on the second elastic structure; the pushing ring rotates, the bump components move in the bump slots to drive the at least two bayonet locks to move outwards along the radial direction, the at least two bayonet locks are disengaged from the clamping flange, and the syringe is pulled out along the axial direction; after the syringe is released, under the action of the second elastic structure, the pushing ring rotates and is restored.

2. The device for rapidly loading and releasing a syringe according to claim 1, wherein sides, facing away from the limiting flange, of the at least two clamping portions are ramps.

3. The device for rapidly loading and releasing a syringe according to claim 1, wherein first chamfers are disposed on two ends of each side, facing away from the limiting flange, of the at least two clamping portions.

4. The device for rapidly loading and releasing a syringe according to claim 1, wherein a socket used for insertion of the syringe is disposed on the injection head, and a ring of the socket and the at least two bayonet locks located, the pushing ring, and the guide sleeve are disposed based on a same axis; loading slots are respectively disposed on locations, corresponding to the at least two bayonet locks, on an edge of the socket, and the at least two clamping portions enter the injection head through the loading slots.

5. The device for rapidly loading and releasing a syringe according to claim 4, wherein first chamfers are disposed on two ends of each of the at least two clamping portions, and second chamfers matching the first chamfers are disposed on two ends of each of the loading slots.

6. The device for rapidly loading and releasing a syringe according to claim 1, wherein sides, facing the injection head, of the at least two clamping portions are first ramps, and second ramps matching the first ramps are disposed on ends of the at least two bayonet locks.

7. The device for rapidly loading and releasing a syringe according to claim 1, wherein the bump slots are disposed on the injection head, each of the at least two bayonet locks corresponds to one of the bump slots, the at least two bayonet locks are installed inside the bump slots, one end of each of the at least two bayonet locks stretches into one of the corresponding bump slots and the first elastic structures are disposed between the at least two bayonet locks and the bump slots, and the at least two bayonet locks move along the bump slots along the radial direction.

8. The device for rapidly loading and releasing a syringe according to claim 1, wherein the bump components comprise embossed bearing shafts disposed on the sides of the at least two bayonet locks and bearings sleeved on the embossed bearing shafts.

9. The device for rapidly loading and releasing a syringe according to claim 1, wherein the bump slots are disposed along a circumferential direction, and each bump slot gradually deviates from a center from an initial end to a tail end.

10. The device for rapidly loading and releasing a syringe according to claim 1, wherein limiting bosses are disposed on the end, stretching into the guide sleeve, of the pushing ring, guide sleeve limiting slots are disposed inside the guide sleeve, the limiting bosses stretch into the guide sleeve limiting slots, the pushing ring rotates relative to the guide sleeve, and the limiting bosses slide along the guide sleeve limiting slots, to limit a range of an angle by which the pushing ring rotates.

11. The device for rapidly loading and releasing a syringe according to claim 1, wherein the second elastic structure is a torsion spring, the torsion spring is sleeved on an outer circle of the pushing ring, one end of the torsion spring is fixed onto the pushing ring, and the other end is fixed onto the guide sleeve.

12. The device for rapidly loading and releasing a syringe according to claim 1, wherein the at least two clamping portions comprise two clamping portions that are disposed symmetrically along a circumferential direction, and wherein the at least two bayonet locks comprise two bayonet locks that are disposed symmetrically along a circumferential direction are disposed on the injection head.

13. The device for rapidly loading and releasing a syringe according to claim 12, wherein two backing pins are further disposed on the injection head, the backing pins and the two bayonet locks are disposed on the same circle, and the backing pins are disposed between adjacent bayonet locks; a second set of slots are disposed on the injection head, one end of each of the backing pins stretches into one of the corresponding second set of slots, third elastic structures are disposed between the backing pins and the second set of slots, and the other end of each of the backing pins stretches out from one of the corresponding second set of slots; and during releasing of the syringe, after the two bayonet locks move outwards, the syringe is moved outwards along an axial direction, the two clamping portions push to enable the backing pins to move outwards, the syringe is disengaged from the injection head, and then the backing pins are restored under the action of the third elastic structures.

14. The device for rapidly loading and releasing a syringe according to claim 13, wherein releasing slots are further disposed on locations, corresponding to the backing pins, on an edge of the socket on the injection head, and during releasing, after pushing to enable the backing pins to move outwards, the at least two clamping portions slide out from the injection head along the releasing slots.

15. The device for rapidly loading and releasing a syringe according to claim 1, wherein the at least two clamping portions comprise four clamping portions, the four clamping portions are evenly arranged on the syringe along an axial direction, wherein the at least two bayonet locks comprise two bayonet locks that are disposed on the injection head, and the two bayonet locks face two clamping portions of the four clamping portions that are disposed opposite to each other.

* * * * *